United States Patent [19]

Meidert et al.

[11] 4,277,606

[45] Jul. 7, 1981

[54] 8-OXO-5,6,7,8-TETRAHYDRO-2-QUINOLONE AND PROCESS FOR THE PREPARATION THEREOF

[75] Inventors: Helmut Meidert, Frankfurt am Main; Wilfried Pressler, Kelkheim; Werner H. Müller, Eppstein, all of Fed. Rep. of Germany

[73] Assignee: Hoechst Aktiengesellschaft, Frankfurt am Main, Fed. Rep. of Germany

[21] Appl. No.: 127,566

[22] Filed: Mar. 6, 1980

[30] Foreign Application Priority Data

Mar. 8, 1979 [DE] Fed. Rep. of Germany ....... 2909035

[51] Int. Cl.$^3$ ........................................... C07D 215/24
[52] U.S. Cl. ................................... 546/157; 260/155
[58] Field of Search ......................................... 546/157

[56] References Cited

U.S. PATENT DOCUMENTS

| 3,400,130 | 9/1968 | Shroff | 546/157 |
| 4,226,997 | 10/1980 | Meidert et al. | 546/157 |

FOREIGN PATENT DOCUMENTS 46-38790 11/1971 Japan ....................................... 546/157

*Primary Examiner*—Donald G. Daus
*Assistant Examiner*—Diana G. Rivers
*Attorney, Agent, or Firm*—Curtis, Morris & Safford

[57] ABSTRACT

8-Oxo-5,6,7,8-tetrahydro-2-quinolone is a novel compound which is prepared by hydrolyzing the hydrochloride of the corresponding 8-chloro compound or the hydrobromide of the corresponding 8-bromo compound to give the corresponding 8-hydroxy compound, and dehydrogenating the latter one.

6 Claims, No Drawings

8-OXO-5,6,7,8-TETRAHYDRO-2-QUINOLONE AND PROCESS FOR THE PREPARATION THEREOF

Subject of the present invention is 8-oxo-5,6,7,8-tetrahydro-2-quinolone of the formula

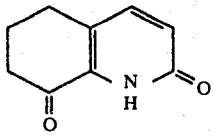

which has not been described hitherto in the literature.

A further subject of the invention is a process for the preparation of 8-oxo-5,6,7,8-tetrahydro-2-quinolone, which comprises hydrolyzing 8-chloro-5,6,7,8-tetrahydro-2-quinolone hydrochloride or 8-bromo-5,6,7,8-tetrahydro-2-quinolone hydrobromide with water at 50° to 100° C. to form the corresponding 8-hydroxy compound, subsequently neutralizing the aqueous solution, removing the water of crystallization from the 8-hydroxy-5,6,7,8-tetrahydro-2-quinolone trihydrate obtained, and dehydrogenating the anhydrous compound in a solvent with manganese dioxide to give 8-oxo-5,6,7,8-tetrahydro-2-quinolone. The complete course of the reaction is illustrated by the following scheme (X being Cl or Br):

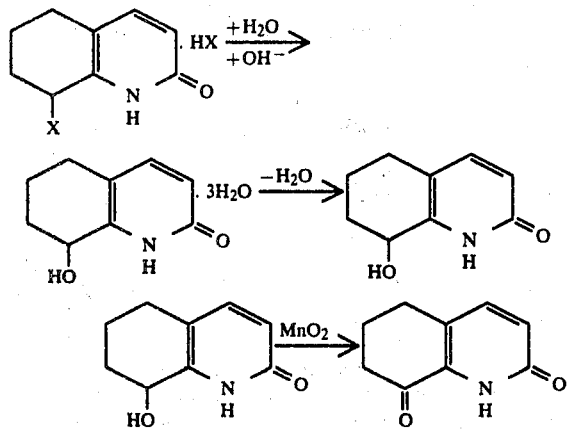

Because of its properties as a cyclic ketone, the 8-oxo-5,6,7,8-tetrahydro-2-quinolone of the invention is the key compound for various consecutive products. It is furthermore possible to convert the compound of the invention to the 8-hydroxy-3,4-dihydro-2-quinolone by simple isomerization:

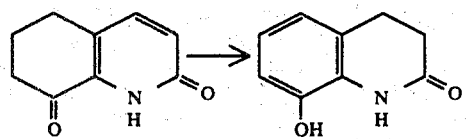

This heterocyclic phenol is especially interesting, because aromatic heterocyclic compounds are of increasing importance as coupling components for disperse dyes (see for example Rys-M. Zollinger, Leitfaden der Farbstoffchemie, Verlag Chemie, Weinheim, 1970, p. 63). Because of its high melting point, however, 8-hydroxy-3,4-dihydro-2-quinolone is an excellent coupling component for the manufacture of polyester dyes.

Starting materials for the preparation of the ketone of the invention are 8-chloro-5,6,7,8-tetrahydro-2-quinolone hydrochloride or 8-bromo-5,6,7,8-tetrahydro-2-quinolone hydrobromide, which are hydrolyzed with the 4- to 8-fold amount of water, at a temperature of from 50° to 100° C., preferably 80° to 100° C., to form 8-hydroxy-5,6,7,8-tetrahydro-2-quinolone which, after cooling of the neutralized solution (neutralization for example by means of ammonia) precipitates in crystallized form as trihydrate. In order to prepare the ketone of the invention, it is however required to oxidize the anhydrous 8-hydroxy-5,6,7,8-tetrahydro-2-quinolone with manganese dioxide. The necessary dehydration of the trihydrate formed first is generally carried out by distillation removal of the hydration water as azeotropic mixture with, for example, butyl acetate, chloroform, butanol, toluene or cyclohexanone. Butyl acetate and cyclohexanone have proved to be especially suitable as agents for forming an azeotropic mixture (=water entrainers), because they allow particularly economic operations due to their good dissolving power, relatively high boiling point and minimal miscibility with water.

Dehydrogenation of the 8-hydroxy-5,6,7,8-tetrahydro-2-quinolone to form the 8-oxo-5,6,7,8-tetrahydro-2-quinolone of the invention is carried out by means of manganese dioxide in a solvent, generally at 20° to 100° C., preferably 30° to 60° C. Suitable solvents are for example chloroform, dichloroethane, butyl acetate, dioxan, butanol or cyclohexanone. It is especially advantageous to use butyl acetate, cyclohexanone or chloroform as water entrainer for dehydration of the trihydrate, and subsequently to employ this entrainer as solvent for the dehydrogenation of the anhydrous hydroxy compound without previous isolation thereof.

The starting compounds for the process of the invention, that is, 8-chloro-5,6,7,8-tetrahydro-2-quinolone hydrochloride or 8-bromo-5,6,7,8-tetrahydro-2-quinolone hydrobromide, are prepared as described in German Offenlegungsschrift No. 28,40,437 in the following manner:

3,4,5,6,7,8-hexahydro-2-quinolone, which is easily obtainable from cyclohexanone and acrylonitrile (see J. Org. Chem. 29, 2781 (1964)), is reacted with chlorine or bromine in an inert solvent at a temperature of from 10° to 50° C., and after the addition of halogen is complete, the reaction mixture is heated to a temperature of from 60° to 80° C. The reaction proceeds according to the following scheme (X=Cl or Br):

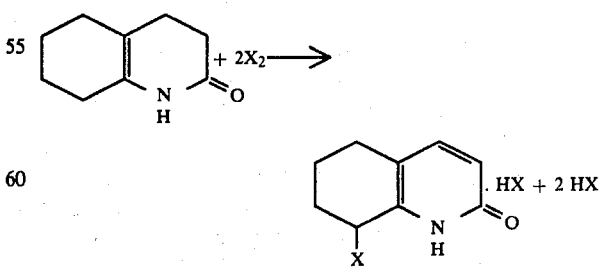

1 to 4 Mols of halogen are preferably used per mol of starting compound.

Suitable solvents for the starting compound to be halogenated are in principle solvents inert to the reactants, for example chlorinated hydrocarbons, glacial acetic acid, dimethyl formamide. Preferred are chlorinated hydrocarbons such as 1,2-dichloroethane, methylene chloride, chloroform or carbon tetrachloride.

The concentration of starting compound in the solvent is generally chosen in such a manner that one part by weight of starting compound is dissolved in 5 to 12 parts by volume of the corresponding solvent.

The rate of introducing gaseous chlorine or adding dropwise the bromine is preferably from 0.2 to 0.6 mol of halogen per mol of dissolved starting compound and per hour. The chlorine is generally introduced without dilution directly as a current into the solution of the starting compound, while the bromine is advantageously diluted preliminarily with the solvent.

During the period of after-heating to 60°–80° C., the 8-chloro-5,6,7,8-tetrahydro-2-quinolone hydrochloride or the 8-bromo-5,6,7,8-tetrahydro-2-quinolone hydrobromide precipitates in crystallized form from the solution.

Preferably, 8-chloro-5,6,7,8-tetrahydro-2-quinolone hydrochloride is used as starting material for the preparation of the 8-oxo-5,6,7,8-tetrahydro-2-quinolone of the invention.

The following examples illustrate the invention.

EXAMPLE 1

110 g (0.5 mol) of 8-chloro-5,6,7,8-tetrahydro-2-quinolone hydrochloride are heated with 500 ml of water to about 90° C. with agitation, thus obtaining after a short time a transparent solution which is then neutralized with 75 ml of concentrated ammonia. After cooling of the solution, 105 g of 8-hydroxy-5,6,7,8-tetrahydro-2-quinolone trihydrate are isolated having a melting point of 192° C., which correspond to a yield of 85.7% of theory. 105 g (0.48 mol) of trihydrate are heated with 2 liters of chloroform while stirring, the hydration water is removed in the form of an azeotropic mixture, and the chloroform phase of the distillate is recycled to the flask. After this operation is complete, 350 g of manganese dioxide (precipitated in an active form) are added to the chloroform solution in portions and in such a manner that the reaction temperature does not exceed 40° C. Intense agitation is continued at this temperature for 3 hours. Subsequently, the batch is separated from the manganese dioxide, the chloroform is distilled off, and 65 g of light brown 8-oxo-5,6,7,8-tetrahydro-2-quinolone, corresponding to a yield of 83% of theory, are isolated, which after recrystallization from cyclohexanone has a melting point of 253° C. in a closed vial.

EXAMPLE 2

(a) Isomerization of 8-oxo-5,6,7,8-tetrahydro-2-quinolone to form 8-hydroxy-3,4-dihydro-2-quinolone 16.3 g (0.1 mol) of 8-oxo-5,6,7,8-tetrahydro-2-quinolone are heated for 30 minutes to 150° C. in 375 ml of anisol together with 5 g of palladium (5%) on carbon, and the still hot solution is immediately filtered off from the catalyst. The colorless, finely crystalline isomerization product 8-hydroxy-3,4-dihydro-2-quinolone rapidly precipitating in this operation is obtained in an amount of 12.1 g, corresponding to a yield of 74.2% of theory, m.p. 201° C.

(b) Coupling of 8-hydroxy-3,4-dihydro-2-quinolone 3.5 g of 3-nitro-aniline are suspended in 15 ml of glacial acetic acid and, after addition of 15 ml of concentrated hydrochlorid acid, diazotized at 0° C. with a solution of 2.5 g of sodium nitrite in 5 ml of water. Subsequently, the solution is diluted with 25 ml of 2-methoxy-ethanol having a temperature of 0° C. 4.1 g of 8-hydroxy-3,4-dihydro-2-quinolone and 30 g of potassium acetate are dissolved in 200 ml of 2-methoxy-ethanol, and cooled to 8°–10° C., and the diazonium solution is then slowly added dropwise. After stirring for a further 10 minutes, the mixture is slowly poured into 1 liter of water, the precipitate is suction-filtered, washed and dried. The dyestuff (4.5 g) so obtained has the following formula

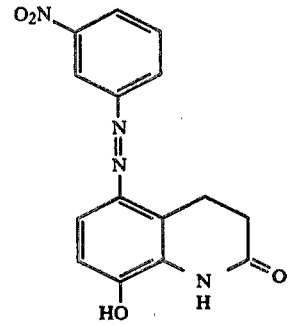

The orche-colored product dissolves in organic solvents such as tetrachloroethylene while taking on a yellow shade. Finely dispersed, the dyestuff yields on synthetic polyethylene terephthalate fabrics yellow dyeings having a good fastness to sublimation, washing and light.

What is claimed is:

1. 8-Oxo-5,6,7,8-tetrahydro-2-quinolone of the formula

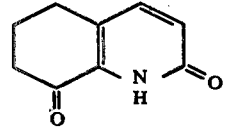

2. A process for the preparation of 8-oxo-5,6,7,8-tetrahydro-2-quinolone, which comprises hydrolyzing 8-chloro-5,6,7,8-tetrahydro-2-quinolone hydrochloride or 8-bromo-5,6,7,8-tetrahydro-2-quinolone hydrobromide with water at 50° to 100° C. to form the corresponding 8-hydroxy compound, subsequently neutralizing the aqueous solution, removing the water of crystallization from the 8-hydroxy-5,6,7,8-tetrahydro-2-quinolone trihydrate obtained, and dehydrogenating the anhydrous compound in a solvent with manganese dioxide to give 8-oxo-5,6,7,8-tetrahydro-2-quinolone.

3. The process as claimed in claim 2, wherein the hydrolysis is carried out at 80° to 100° C.

4. The process as claimed in claim 2 or 3, which comprises obtaining the anhydrous 8-hydroxy-5,6,7,8-tetrahydro-2-quinolone from the trihydrate thereof by distillation removal of the water of crystallization by means of a water entrainer.

5. The process as claimed in claim 4, which comprises using the same substance as water entrainer for the dehydration and as solvent for the subsequent dehydrogenation of the 8-hydroxy-5,6,7,8-tetrahydro-2-quinolone.

6. The process as claimed in claim 5, which comprises using chloroform, cyclohexanone or butyl acetate as water entrainer and as solvent.

* * * * *